(12) United States Patent
Bak et al.

(10) Patent No.: US 6,781,045 B2
(45) Date of Patent: Aug. 24, 2004

(54) GUZMANIA PLANT NAMED 'BASIC'

(75) Inventors: Elly Bak, Rijsenhout (NL); Nicolaas D. M. Steur, Oude Niedorp (NL)

(73) Assignee: Corn. Bak. B.V., Assendelft (NL)

( * ) Notice: Subject to any disclaimer, the term of this patent is extended or adjusted under 35 U.S.C. 154(b) by 253 days.

(21) Appl. No.: 10/242,454

(22) Filed: Sep. 13, 2002

(65) Prior Publication Data

US 2004/0055031 A1 Mar. 18, 2004

(51) Int. Cl.$^7$ .............................. A01H 5/00; A01H 1/00; A01H 1/02
(52) U.S. Cl. ....................... 800/323; 800/298; 800/260; Plt./371
(58) Field of Search ................................. 800/323, 260, 800/298; Plt./371

(56) References Cited

PUBLICATIONS

Benzing, David H., The Biology Of The Bromeliads, Mad River Press, Inc., Eureka (1980).
Rauh, Werner, Bromelien, Verlag Eugen Ulmer, Stuttgart (1981).
Zimmer, Karl, Bromelien, Verlag Paul Parey, Berlin (1986).

*Primary Examiner*—Kent Bell
(74) *Attorney, Agent, or Firm*—Foley & Lardner

(57) ABSTRACT

Guzmania cultivar 'Basic' is solid, tenable, medium-sized and long lasting with a star shaped purple inflorescence.

4 Claims, 1 Drawing Sheet

(1 of 1 Drawing Sheet(s) Filed in Color)

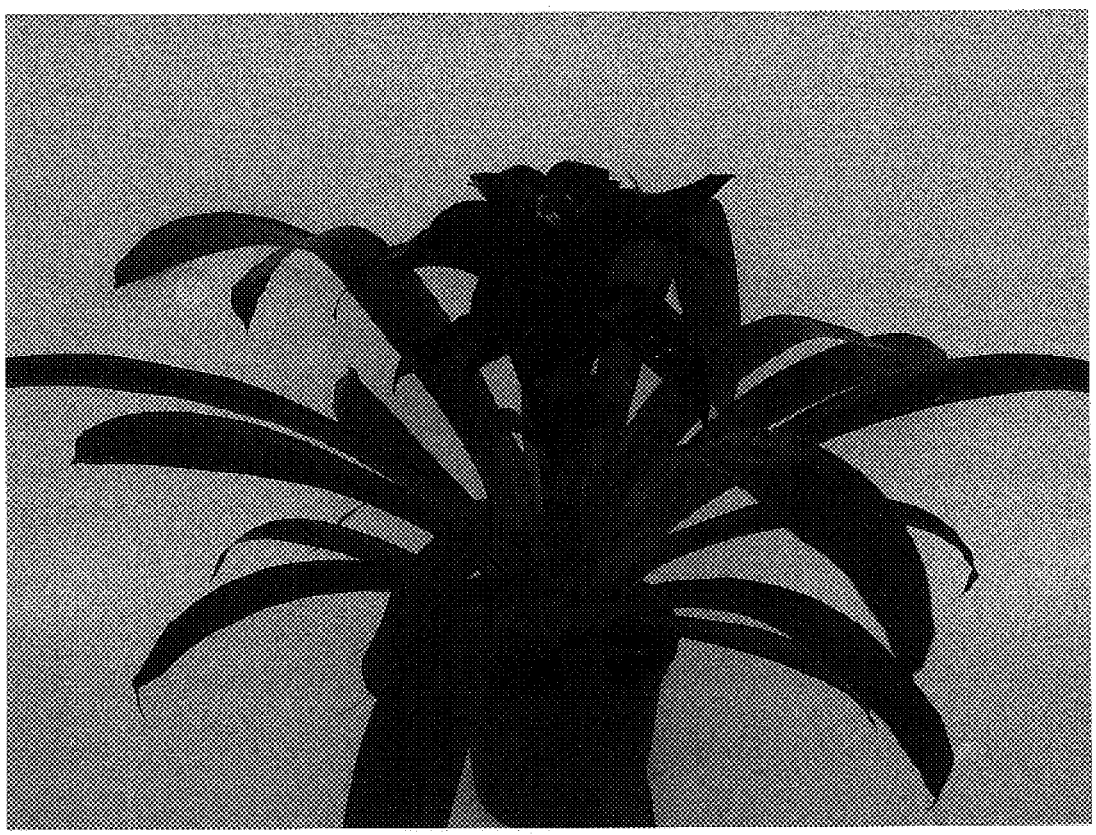

GUZMANIA PLANT NAMED 'BASIC'

FIELD OF THE INVENTION

The present invention relates to a new, distinct and stable plant of Guzmania that is a hybrid, hereinafter referred to as 'Basic'. The present invention relates to seeds which are Guzmania cultivar 'Basic' as well as plants and plant parts produced from these seeds which have all the morphological and physiological characteristics of the Guzmania cultivar 'Basic'. The present invention also relates to methods for producing these seeds and plants. Furthermore, the present invention relates to a method of producing progeny Guzmania plants by crossing Guzmania cultivar 'Basic', as the male or female parent, with another Guzmania plant and selecting progeny.

BACKGROUND OF THE INVENTION

The new cultivar is a hybrid of the specie *Guzmania lingulata*. Guzmania is a member of the Bromeliaceae family. Guzmania is predominantly epiphytic with a few terrestrial species and is native to the tropics. For the most part, species vary in diameter from 7 or 8 inches to 3 or 4 feet and have rosettes of glossy, smooth-edged leaves.

Floral bracts of Guzmania frequently have brilliant colors and may last for many months. The range of colors for Guzmania is generally from yellow through orange but may also include flame red and red-purple. White or yellow, tubular, three-petalled flowers may also appear on a stem or within the leaf rosette but are usually short-lived.

Guzmania may be advantageously grown as pot plants for greenhouse or home use. Typically, the plants are shaded from direct sunlight. During the spring to autumn period, the central vase-like part of the leaf rosette is normally filled with water.

Guzmania is native to tropical America. Leaves of Guzmania are usually formed as basal rosettes which are stiff and entire and in several vertical ranks. Guzmania plants have terminal spikes or panicles which are often bracted with petals united in a tube about as long as the calyx. The ovary is superior and the seeds plumose.

Asexual propagation of Guzmania is frequently done through the use of tissue culture practices. Propagation can also be from offshoots which can be detached from the mother plant and grown in an appropriate soil or bark mixture.

Methods for cultivation and crossing of Guzmania are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag Paul Parey, Berlin (1986); and Rauh, Werner, BROMELIEN, Verlag Eugen Ulmer, Stuttgart (1981).

A Guzmania inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect to their morphological and physiological characteristics.

A need exists for a greater variety of Guzmania cultivars with attractive ornamental features. Additionally, a need exists for additional Guzmania hybrid cultivars that can be easily propagated by seed. The new cultivar was developed through a controlled breeding program and exhibits unique, desirable and stable characteristics.

SUMMARY OF THE INVENTION

The instant invention provides Guzmania plant selections that are solid, tenable, medium-sized and long-lasting. The instant invention also provides Guzmania plant selections with a star shaped deep purple inflorescence.

These and other objectives have been achieved in accordance with the present invention which provides a new cultivar 'Basic' that is a product of a planned breeding program undertaken by the inventors in Assendelft, The Netherlands, in 1996. The male or pollen parent was a selection of *Guzmania lingulata* identified by Code No. 96204128. The female or seed parent was a selection of *Guzmania lingulata* minor identified by Code No. 96204031.

Both parents have a sufficient degree of homozygosity such that the progeny of the cross are genetically and phenotypically uniform. The cultivar 'Basic' therefore can be produced by sexual reproduction by crossing 96204128× 96204031 to produce a population of progeny plants, each of which has the combination of characteristics as herein disclosed for the new cultivar.

Seeds which are cultivar 'Basic' are produced by crossing 96204128×96204031 and are deposited with the American Type Culture Collection (ATCC), 10801 University Boulevard, Manassas, Va. 20110-2209 (Patent Deposit Designation No. PTA-4663). 2500 seeds were deposited with the ATCC on Sep. 10, 2002.

OBJECTS OF THE INVENTION

This invention relates to seeds which produce Guzmania cultivar 'Basic' This invention also relates to Guzmania plants, and parts thereof, having all the physiological and morphological characteristics of Guzmania cultivar 'Basic'. This invention relates to a plant produced from seeds which are Guzmania cultivar 'Basic'. This invention also relates to plant parts, such as pollen, seeds or inflorescence produced by Guzmania cultivar 'Basic'.

This invention relates to a method of producing seed which are Guzmania cultivar 'Basic' by crossing *Guzmania lingulata* selection 96204128 as the male parent with *Guzmania lingulata* minor selection 96204031 as the female parent and the reciprocate cross with 96204031 as the female parent and 96204128 as the male parent and harvesting seeds produced from said crosses.

This invention also relates to a method of producing plants having all the physiological and morphological characteristics of the Guzmania cultivar 'Basic' comprising the steps of (a) crossing *Guzmania lingulata* selection 96204128 as the male parent with *Guzmania lingulata* minor selection 96204031 as the female parent; (b) harvesting seeds produced from said cross; and (c) producing plants from said harvested seeds.

The invention also relates to producing progeny plants from the cross of Guzmania cultivar 'Basic' as the male or female parent, with another Guzmania plant, and selecting progeny plants for this cross.

BRIEF DESCRIPTION OF THE DRAWINGS

The file contains at least one drawing executed in color. Copies of this patent with the color drawing(s) will be provided by the Patent and Trademark Office upon request and payment of the necessary fee.

The photographic drawing shows a whole plant view of the inflorescence and foliage of 'Basic', with colors being as true as possible with illustrations of this type.

DETAILED DESCRIPTION OF THE PREFERRED EMBODIMENTS

The present invention was created by the inventors, Elly Bak and Nicolaas D. M. Steur in 1996, and flowered for the first time in 1999 in Assendelft, The Netherlands.

This invention is directed to a Guzmania plant having all the morphological and physiological characteristics of the cultivar 'Basic' produced from seeds which are the product of the cross of *Guzmania lingulata* selection 96204128 as the male parent with *Guzmania lingulata* minor selection 96204031 as the female parent. Both parents have a sufficient degree of homozygosity such that the progeny of the cross were, and continue to be, phenotypically uniform. The variety 'Basic' therefore can be produced by sexual reproduction by crossing 96204128×96204031 to produce a population of progeny plants each of which has the combination of characteristics as herein disclosed for the new cultivar.

The variety 'Basic' can also be produced by asexually reproducing progeny from the cross of 96204128×96204031 because the combination of characteristics as herein disclosed for the new cultivar 'Basic' are firmly fixed and are retained through successive generations of asexual reproduction. The selection comprising the new variety was chosen after commencement of flowering of the progeny in 1999 in Assendelft, The Netherlands. Sexual and asexual propagation has demonstrated that the combination of characteristics as herein disclosed for the new cultivar 'Basis' as observed in Assendelft, The Netherlands, are firmly fixed and are retained through successive generations of asexual reproduction.

'Basic' is particularly characterized by the following characteristics:
1. solid, tenable, medium-sized growth habit in a funnel-form rosette measuring approximately 28 cm in height when flowering;
2. numerous leaves, each approximately 30–46 cm in length;
3. approximately 10 scape bracts and 14 primary bracts;
4. star-shaped inflorescence;
5. deep purple primary and scape bracts, RHS 59A; and
6. long-lasting habit.

'Basic' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar.

For example, substantial differences in plant height and diameter, and the number of leaves, can result depending on the size of the plant at the time flowering is induced by acetylene treatment. Since treatment with acetylene to induce flowering disrupts normal watering and fertilization regimens, acetylene treatment of relatively smaller plants adversely affects the growth of the plant.

The following traits have been repeatedly observed and in combination distinguish 'Basic' as a new and distinct cultivar. These observations, measurements and descriptions were taken for 'Basic' plants grown under the following greenhouse conditions in Assendelft, The Netherlands.

The new cultivar flowers approximately 13 weeks after treatment with Acetylene.

The closest comparison cultivar is Guzmania 'Classic' (Co-pending U.S. patent application Ser. No. 10/242,624. The most important difference between 'Basic' and 'Classic' is the color of the inflorescence. 'Basic' has a deep purple inflorescence, while 'Classic' has a red inflorescence.

In the following description, color references are made to The Royal Horticultural Society Colour Chart (RHS). Observations, measurements and descriptions of Guzmania 'Basic' were made under Dutch greenhouse conditions.

Plant:
    Form—Funnel form rosettes.
    Height—Approximately 28 cm high (flowering).
    Diameter—Approximately 60 cm.
    Growth habit—Stemless.

Foliage:
    Size—Approximately 30–46 cm in length, 3–6 cm in width.
    Shape—Linear.
    Surface texture—Smooth.
    Color—Upperside: between RHS 137 A and RHS 137 B; underside: RHS 137 C (color dependent on environmental conditions).
    Apex—Acute.

Flowers:
    Borne—Erect stalks.
    Shape of inflorescence—Round spike (like head).
    Size of the inflorescence—Approximately 8 cm in length; approximately 20 cm in diameter.
    Individual petals—Approximately 5.5 cm in length; 0.5 cm in width; color RHS 155 D and 17 C.
    Number of flowers per inflorescence—Approximately 40.
    Lastingness of the inflorescence—A full grown plant can produce an inflorescence containing approximately 40 flowers and can bloom anytime throughout the year beginning approximately 13 weeks after natural induction or induction with acetylene. Each flower blooms for one day and the total length of blooming of the whole inflorescence is 5 weeks.

Disease/pest resistance/susceptibility: No information to date.

Bracts:
Scap bract: Approximately 17 cm (lowest) to approximately 14 cm just below the primary bracts in length; approximate 2–4 cm in width; approximately 10 in number; lanceolate shape; smooth texture; margin entire; acute apices; color at apex, between RHS 137 A and 137 B; at scape RHS 150 B and RHS 59 A in the middle.
Primary bract: Approximately 14 cm (lowest) to approximately 8 cm at the top in length; approximately 2–5 cm in width; approximately 14 in number; lanceolate shape; smooth texture; margin entire; acute apices; color RHS 59 A and RHS 150 B at the scape.

Floral bract: 5.5 cm in length; approximately 0.5 cm in width; approximately 40 in number; lanceolate shape; smooth texture; margin entire; acute apices; color RHS 155 D and RHS 17 C.

What is claimed is:

1. A Guzmania plant designated cultivar 'Basic' obtained from seed having American Type Culture Collection (ATCC) Patent Deposit Designation No. PTA-4663.

2. Guzmania seed having ATCC Patent Deposit Designation No. PTA-4663.

3. Plant parts obtained from the Guzmania plant of claim 1.

4. A method of producing Guzmania progeny plant comprising of the steps of (a) crossing Guzmania cultivar 'Basic' produced from seed accorded ATCC Patent Deposit Designation No. PTA-4663 as a male or female parent with another Guzmania plant and (b) selecting progeny.

* * * * *